United States Patent [19]

Lorenz et al.

[11] Patent Number: 5,156,601
[45] Date of Patent: Oct. 20, 1992

[54] TACKY, HYDROPHILIC GEL DRESSINGS AND PRODUCTS THEREFROM

[75] Inventors: Donald H. Lorenz, Basking Ridge, N.J.; Connie C. Lee, Newtown, Pa.

[73] Assignee: Hydromer, Inc., Whitehouse, N.J.

[21] Appl. No.: 672,357

[22] Filed: Mar. 20, 1991

[51] Int. Cl.$^5$ .................. A61F 13/00; A61F 13/02; A61L 15/00; C08L 15/00

[52] U.S. Cl. .................. 604/307; 604/304; 602/41; 602/42; 602/43; 602/46; 602/48; 602/58; 424/445; 523/111

[58] Field of Search .................. 523/111, 112, 122; 128/156; 604/369, 304, 307, 358, 368, 369; 602/41–43, 46, 48; 424/445

[56] References Cited

U.S. PATENT DOCUMENTS

| | | |
|---|---|---|
| 4,210,633 | 7/1980 | Takruri et al. . |
| 4,265,798 | 5/1981 | Mishra ............... 427/341 |
| 4,310,509 | 1/1982 | Berglund et al. . |
| 4,323,557 | 4/1982 | Rosso et al. . |
| 4,492,685 | 1/1985 | Keith et al. . |
| 4,542,012 | 9/1985 | Dell . |
| 4,593,053 | 6/1986 | Jevne et al. . |
| 4,642,267 | 2/1987 | Creasy et al. . |
| 4,646,730 | 3/1987 | Schonfeld et al. . |
| 4,666,437 | 5/1987 | Lambert . |
| 4,769,013 | 9/1988 | Lorenz et al. ............ 128/156 |
| 4,931,282 | 6/1990 | Asmus et al. . |

FOREIGN PATENT DOCUMENTS 107376 2/1984 European Pat. Off. .

OTHER PUBLICATIONS

A. Conix and G. Smets, "Ring Opening in Lactam Polymers", J. Poly. Chem. 13, 221–229 (1955).
H. P. Frank, "The Lactam–Amino Acid Equilibria for Ethylpyrrolidone and Polyvinylpyrrolidone", Journal of Polymer Science 12, 565–576 (1954).
General Aniline & Film Corporation Technical Bulletin 7583–033, "PVP".

Primary Examiner—Randall L. Green
Assistant Examiner—A. Zuttarelli
Attorney, Agent, or Firm—Hoffman & Baron

[57] ABSTRACT

A dressing includes a stable, tacky gel of polyurethane and poly(N-vinyl lactam), the poly(N-vinyl lactam) having a K-value of at least about 60 and mole equivalents of acid groups above about 1.4. The dressing may also include a substrate and various additives incorporated with the gel.

20 Claims, No Drawings

TACKY, HYDROPHILIC GEL DRESSINGS AND PRODUCTS THEREFROM

BACKGROUND OF THE INVENTION

This invention relates to the field of poly(N-vinyl lactam)-urethane gels and more particularly to gels which are skin adhesive and absorbent, which are flexible and contour-conforming, and which can be used in dressings for a variety of applications.

It has been known that polyvinylpyrrolidone (PVP) forms complexes with polyurethanes to yield hydrophilic blends or alloys. U.S. Pat. No. 4,642,267 decribes hydrophilic polymer blends of polyurethane and hydrophilic poly(N-vinyl lactam) prepared in solvent solution to provide slippery coatings when wet and which are water insoluble to some extent once cured by drying. In contrast to the slippery coatings described in U.S. Pat. No. 4,642,267, the dressings of the present invention are tacky gels.

European Patent Application 107,376 describes tacky PVP gels which require the use of ionizing radiation for cross-linking. U.S. Pat. No. 4,646,730 describes a PVP/Silver Sulfadiazine hydrogel dressing in which electron beam radiation is required to cross-link the PVP and form a gel. In addition, magnesium trisilicate, hydrogen peroxide and/or polyacrylic acid are added for color stabilization. It is apparent that there would be an advantage in making tacky skin-adhering gels in the absence of expensive equipment and/or processing.

Ring opening of pyrrolidone groups on PVP was described by H. P. Frank, "The Lactam-Amino Acid Equilibria for Ethylpyrrolidone and Polyvinylpyrrolidone", Journal of Polymer Science 12, 565–576 (1954), and A. Conex and G. Smets, "Ring Opening in Lactam Polymers", J. Poly. Chem. 13, 221–229 (1955). The concept of ring opened pyrrolidone groups is made use of in this invention to unexpectedly attain absorbent and tacky gels.

It is therefore an object of the invention to provide tacky gels having a hydrophilic property.

It is a further object to produce tacky gels without a need for expensive equipment and/or processing.

It is another object to provide tacky gels of poly(N-vinyl lactam) and urethane which can be used in a variety of skin adhesive products.

SUMMARY OF THE INVENTION

Accordingly, there is provided a dressing comprising a stable, tacky hydrophilic gel which comprises a blend of polyurethane or polyurethanes and a poly(N-vinyl lactam) with or without a plasticizer, the poly(N-vinyl lactam) having a K value of at least about 60 and mole equivalents of acid groups of at least about 1.4. The dressing may also include a substrate which is preferably a polymer film, such as a polyurethane or a silicone-polytetrafluoroethylene film, a collagen film, or a woven or non-woven fabric which may be stretchable. The polymer film may also include an additional skin adhesive which may be applied, for example, around the edges on the side to be applied to skin.

The poly(N-vinyl lactam) is preferably a polyvinylpyrrolidone having mole equivalents of acid groups of at least about 2.

The gel dressing is prepared by mixing aqueous poly(N-vinyl lactam) solution and polyurethane in aqueous dispersion at a poly(N-vinyl lactam/polyurethane ratio of from about 0.5/1 to about 8/1, preferably from about 0.75/1 to about 4/1 and a total solids content above about 5 weight percent to form a blend, forming the blend into a dressing and allowing the dressing to cure until a gel dressing is formed.

The gel preferably includes at least one additional ingredient which may be releasable from the gel. Preferably the releasable ingredient is a fragrance or a bio-effecting or body-treating material.

Preferred products for which the dressing may be used are wound and burn dressings, drug delivery systems, antimicrobial interface devices, sports wraps, and cosmetic masks and wraps.

The dressings have the advantage of self-adhesion to the skin but with facile peelability. The gels are stable even in hot water, are capable of absorbing many times their weight in water, and are capable or delivering medicaments externally to the body exactly where desired.

For a better understanding of the present invention, together with other and further objects, reference is made to the following description, and its scope will be pointed out in the appended claims.

DESCRIPTION OF THE PREFERRED EMBODIMENTS

It has been found that poly(N-vinyl lactam) such as polyvinylpyrrolidone (PVP), with a degree of ring opened pyrrolidone groups, forms irreversible hydrophilic gels with certain aqueous dispersed polyurethanes. These gels have a tacky quality so that they can adhere to skin but are peelable. The gels are flexible and transparent or translucent and may be used alone or with various additives. The gels can be used for wound and burn dressings, drug delivery systems, cosmetic face and nail wraps, and other applications where the high heat capacity and heat or cold reservoir/transport capacity of water as part of the hydrophilic gel can be utilized.

Suitable poly(N-vinyl lactams) have a K value of at least about 60, preferably at least about 70, and most preferably from about 80 to about 110.

In the invention, poly N-vinyl lactams containing above certain levels of ring opened pyrrolidone groups, when mixed with certain aqueous dispersed urethanes, form gels which are tacky. The term tacky is intended to mean having the property of being sticky to the touch or adhesive to a degree that the gel is capable of sticking to the skin while being easily removable when removal is desired.

The term poly(N-vinyl lactam) as used herein shall be understood to include homopolymers, copolymers and terpolymers of N-vinyl lactams such as N-vinylpyrrolidone, N-vinylbutyrolactam, N-vinylcaprolactam, and the like, as well as the foregoing prepared with minor amounts, for example, up to about 20 weight percent, of one or a mixture of other vinyl monomers copolymerizable with the N-vinyl lactams. Copolymers or terpolymers of poly(N-vinyl-lactam) may comprise N-vinyl-lactam monomers such as vinylpyrrolidone copolymerized with monomers containing a vinyl functional group such as acrylates, hydroxyalkylacrylates, methacrylates, acrylic acid or methacrylic acid, and acrylamides. Of the poly(N-vinyl lactam) homopolymers, the polyvinylpyrrolidone (PVP) homopolymers are preferred. Of the poly(N-vinyl lactam) copolymers, vinyl pyrrolidone acrylamide copolymers are preferred. A suitable poly(N-vinyl lactam) terpolymer is vinylpyrrolidone, vinylcaprolactam, dimethylaminoethyl methacrylate. A variety of polyvinylpyrrolidones are commercially available. It is important, however, for the poly(N-vinyl lactam) to contain a degree of ring-opened lactam groups.

A lactam may be considered to be a cyclic amide produced from an amino acid through the elimination of a molecule of water from the —COOH and —NH$_2$ groups. A lactam, therefore, contains a —NH—CO— group in a ring. An N-vinyl lactam has a vinyl group at the ring nitrogen and the monomer can be polymerized through the vinyl group. In a ring-opened poly(N-vinyl lactam), the vinyl backbone may be considered to remain essentially intact, but some lactam rings are opened to make available —COOH groups. The availability of these —COOH groups may be measured through base titration to determine the mole equivalents of base per mole of acid groups in a specific poly(N-vinyl lactam). Because the polymer backbone remains essentially intact, different poly(N-vinyl lactams) having the same molecular weight or K-value may have different levels of ring openings. The poly(N-vinyl lactams) useful in forming the gels in the invention have a mole equivalent/mole of acid groups greater than about 1.4, preferably greater than about 2.0. In the absence of opened lactam rings, the gel does not form. The poly(N-vinyl lactams) are preferably of relatively high molecular weight as indicated by a K value above about 60.

Ring opening in poly(N-vinyl lactams) may be effected by heating a solution of the poly(N-vinyl lactam) at a temperature of from about 50° C. to about 120° C., with from about 60° C. to about 100° C. preferred, at pressure from about 15 psi to about 150 psi for from about one half hour to about 10 days, with from about one hour to about 24 hours preferred. The solvent for the solution is preferably aqueous and may include a small amount of a weak base such as dilute ammonium hydroxide or dilute sodium hydroxide to result in a solution which is slightly basic, e.g. having a pH of about 7-9, with about 7-8 or 7-8.5 preferred. If time saving is an important consideration as in commercial operations, ring opening may be carried out, for example, for shorter periods of time in a reactor under conditions of high temperature and pressure, e.g. 200° C. at 50 psi.

To form the gel, the poly(N-vinyl lactam) is mixed or blended with polyurethane. The urethane portion of the blend is based, for example, on ethoxylates of dimethylol propionic acid reacted with either aromatic isocyanates or aliphatic isocyanate such as toluene diisocyanate (TDI), methylene di-p-phenylene isocyanate (MDI) (diphenylmethane-4,4'-diisocyanate), hexamethylene diisocyanate, or dicyclohexylene diisocyanate, to form a prepolymer, reacted with chain extender and then dispersed in water to which triethylamine is added to partially neutralize the acid function. Urethane resins are commercially available, for example, NeoRez R-940 (Imperial Chemical Industries, Ltd.) and Sancure 847 (Sanncore Industries, Inc.). The polyurethane is preferably in the form of an aqueous dispersion.

The gel may be prepared by dissolving the poly(N-vinyl lactam) such as polyvinylpyrrolidone in aqueous solution, then adding an aqueous dispersed polyurethane with sufficient agitation to attain a homogenous mixture or blend with at least 5% total solids, i.e., at least 5 weight percent total PVP and polyurethane. The solvent used for the gel preparation is preferably substantially aqueous. For example, the gels may be prepared in water or in hydroalcohols such as water/isopropyl alcohol and water/ethanol. The gels form at a ratio of PVP/urethane of from about 0.5/1 to about 8/1, preferably from about 0.75/1 to about 4/1, at a total solids of at least about 5%. At higher PVP to urethane ratios gels are formed but are weaker and may contain uncomplexed PVP which will leach out in water. At lower solids levels or when the PVP has a K below about 60, gels may form but they can be reversed in hot water. The blend may be allowed to cure for a time of from about 15 seconds to about 2 hours. The time and temperature for curing are not critical. For purposes of convenience, ambient temperature may be used but the time can be shortened at elevated temperatures. The term gel is intended to mean viscous or semi-solid and jelly-like.

The preferred gels are stable and therefore irreversible and water insoluble, even in boiling water or alcohol. The gels can be sterilized by radiation or steam sterilization. The gels are hydrophilic and capable of absorbing many times their weight in water or at least twice their weight in water. For practical application as described herein, a gel absorbs, for example, from about 25 to about 40 times its dry weight in water. The gel material may be considered to absorb fluid based on the ratio of PVP/urethane. For example, at a ratio of PVP/urethane of about 0.75/1 to 1/1, the gel absorbs about 29 times its dry weight (i.e. solids weight) in water; at about 3/1, it can absorb about 38 times its dry weight in water.

While the exact nature of the mechanism by which the gel forms is not known, and while it is not intended to be bound by theory, it is believed to be caused by pervasive and tight hydrogen bonds between chains. The presence of the ring-opened pyrrolidones, in some undetermined way, plays an imperative role in achieving this goal.

Glycerine in an amount of from about 5 to about 50 weight percent, preferably from about 10 to about 30 weight percent may be added to the gel preparation to increase tack and pliability after drying. The glycerine is preferably mixed into the PVP solution prior to adding urethane dispersion. Propylene glycol may also be used.

Many different types of additional materials may be incorporated into the gels including organic salts, inorganic salts at low levels, alcohols, amines, polymer latices, fillers, surfactants, pigments, dyes, fragrances and so forth as long as they do not interfere with gel formation. Many of these materials can be releasable from the gel.

The gels of this invention are especially useful as carriers for a wide variety of releasable biologically active substances having curative or therapeutic value for human or non-human animals. Included among the biologically active materials which are suitable for incorporation into the gels of the invention are hypnotics, sedatives, tranquilizers, anti-convulsants, muscle relaxants, analgesics, antipyretic agents, anti-inflammatory agents, local anesthetics, antispasmodics, antiulcer agents, antivirals, antibacterials, antifungals, sympathomimetic agents, cardiovascular agents, antitumor agents, and so forth. A biologically active substance is added in pharmaceutically active amounts.

Particularly preferred as biologically active additives are nitroglycerine, scopalamine, pilocarpine, phenylpropanolamine, and theophyline; also antimicrobials tetracycline, neomycin, oxytetracycline, triclosan, sodium cefazolin, silver sulfadiazine, and also salicylates such as methylsalicylate and salicylic acid, nicotinates such as methyl nictoninate, capsicum and benzocaine. When the gel is to be used, for example, for cosmetic treatment, hydrating agents such as sodium pyrrolidine carboxylic acid may be added. For a hydrating purpose, however, the large amount of water alone which can be absorbed by the hydrophilic gel serves a hydrating function to the skin.

Water soluble and water insoluble additives such as those described above may be initially mixed with the aqueous solvent before the gel preparation is begun, may be mixed with the aqueous solution of poly(N-vinyl lactam) or mixed with the aqueous dispersed polyurethane during the gel preparation. Water soluble ingredients are preferably mixed in with the PVP prior to admixing with urethane. Many water insoluble ingredients can be mixed with urethane prior to adding to PVP. One can also emulsify water insolubles by adding surfactants to either the PVP or urethane. Alternatively, additives may be similarly mixed into the gel preparation after the poly(N-vinyl lactam) is blended with the polyurethane. Additives may also be applied to the surface of a gel dressing, for example, by spraying, dipping, brushing or rolling.

The gel may be used to make adhesive, absorbent dressings and other products. To obtain the products of the invention, the gel may be provided with at least one substrate or backing and a release liner. To form a dressing, the gel is put on a substrate and covered with a release liner to prevent the gel from sticking to itself thereby forming a sandwich structure with the gel located between a substrate and a release liner. The dressing may also be provided in rolled-up form so that the substrate itself acts as a release liner. In any case, the release liner is removed before the gel is applied to skin. The substrate may fulfill one or several functions including providing reinforcement, providing a gas and liquid barrier, providing a support with gas and liquid permeability, providing protection for the gel and the area of treatment, etc. The substrate may be chosen to supply the desired function(s) and characteristics of the various substrates, e.g. permeability, impermeability, semipermeability, stretchability, etc., are known to those skilled in the art.

The gel may be coated or spread onto a backing or substrate by any means known in the art. The gel can be combined with and adhered to a virtually unlimited variety of substrates or backings including resins, metal foils, woven and non-woven webs of natural and synthetic fibers, etc. A backing which provides gas and liquid barrier properties may be a polymer film such as polyurethane. Desirable composites with the gel may also be made using films of polyvinyl alcohol, polyvinylidene chloride or a silicone-polytetrafluoroethylene interpenetrating polymer membrane or film which is commercially available as Silon (BioMed Sciences, Inc.). When the gel has a barrier substrate of this type, the resulting structure has particular utility as a wound and burn dressing. Moisture is kept in and excess exudate is absorbed to promote healing but bacteria are prevented from entering the wound or burn area, and microbial stasis may be maintained through the incorporation of an anti-microbial agent into the gel to prevent infection. For ease of use, the tacky gel on a backing is covered with a release liner which may be a silicone coated film or polyethylene.

The gel may be coated onto the backing so that the gel occupies all or part of the backing surface. If the gel occupies part of the backing surface, non-gel coated areas of the backing may be provided with an additional adhesive. A dressing of this type is positioned on the skin so that the additional skin adhesive comes into contact with intact skin while the absorbent adhesive gel contacts a wound. The additional adhesive provides a dressing with staying power when the absorbent gel has become substantially saturated with wound exudate thus losing some of its adhesiveness through a dilution effect.

A dressing with a polymer or collagen film backing can also be used to anchor to the skin medical devices which are partially inserted into the body such as catheters and tubes. The area where such devices enter the body provide an interface for the entry of bacteria and other infectious agents. The gel of the invention with an appropriate backing, and optimally containing an anti-microbial, is capable of an adhesive effect which keeps the medical device in place while preventing infection at the insertion site. The gel and backing structure can also be punctured with the medical device to provide a more secure entry site.

A gel structure with a polymer film backing is also useful as a burn blanket for serious burns particularly in emergency situations. The wrap can serve the function of cooling the burned area through the heat sink effect of water in the hydrophilic gel, while preventing infection through a barrier effect of a substrate and/or anti-microbial additives incorporated into the gel.

In another embodiment, the gel may be incorporated with a flexible and permeable backing such as a scrim which may be woven or non-woven fabric and which may be stretchable. When medicaments, for example methylsalicylate, nicotinates such as methyl nicotinate, or capsaicin, either alone or in combination, are incorporated into the gel, this structure has particular usefulness as a stretchable sports wrap.

In still another embodiment, the gel may be used in cosmetic preparations such as face masks and nail wraps. The gel serves a hydrating function with or without a backing and a cosmetic effect may be enhanced with the incorporation of other ingredients. A kit for a cosmetic gel may comprise a ready-made gel or two components: a poly(N-vinyl lactam) component and a polyurethane component. Other cosmetic agents such as hydrating agents, fragrances, etc. can also be supplied to the ready-made gel or to either component. For use, the components may be mixed and applied. The gel advantageously can be easily peeled off after use. It shall be understood that the term cosmetic means a preparation intended to enhance or improve physical appearance.

In a further embodiment, fragrances may be incorporated into the gel. When the gel is kept moist in a suitable vented container, the fragrance is slowly released as an air freshener.

The following examples are intended to illustrate but not limit the invention. In the following examples, the K value represents a function of molecular weight. The K value is derived from viscosity measurements and is calculated according to Fikentscher's formula described by Kline, G. M., "Polyvinylpyrrolidone", Modern Plastics p 157 (Nov. 1945) and is also described in General Aniline & Film Corporation Technical Bulletin 7583-033. Finkentscher's formula for calculating K-value is as follows:

$$\frac{\log \eta^{rel}}{c} = \frac{75 K_0^2}{1 + 1.5 K_0 c} + K_0$$

$K = 1000 K_0$ where $c$=concentration in g/100 ml solution $\eta^{rel}$ = viscosity of the solution compared with solvent.

At the same K-value or molecular weight, the level of ring opened poly(N-vinyl lactam) is an important consideration in determining whether a tacky gel forms.

EXAMPLE 1

A K-92 PVP was titrated with base. The results showed that the PVP had 1.4 mole equivalents/mole of acid groups. Attempts to form a tacky gel using this PVP were unsuccessful. This PVP, when combined with polyurethane, forms a blend which is slippery rather than tacky when formed into a coating or sheet.

EXAMPLE 2

The PVP of Example 1 was heated in water at 60° C. for eight days, then at 95° C. for eight hours. This material, when titrated with base, showed 2.15 mole equivalents/mole of acid groups and formed a tacky, non-reversible gel at a ratio of 1 PVP/1 urethane at 20% solids.

EXAMPLE 3

A commercial PVP (Kollidon 90, BASF), having a K-value of 93 was titrated with base and showed 5 mole equivalents/mole of acid groups. When mixed with urethane, this PVP formed a hydrophilic, tacky gel.

EXAMPLE 4

A PVP (Luviskol, BASF) having a K-value of 93 was titrated with base and showed less than 1 mole equivalent/mole of acid groups. Attempts to form a gel using this PVP with urethane were unsuccessful. This PVP, when combined with polyurethane, forms a blend which is slippery rather than tacky.

EXAMPLE 5

To a beaker containing 50 grams of a 20% solution of PVP described in Example 3 was added 17.7 grams of distilled water with agitation. When the PVP and water were thoroughly mixed, the agitation was lowered to low shear and NeoRez R-940 water dispersed urethane (Imperial Chemical Industries, Ltd.) was added (32.3 gms at 31% solids). Mixing was continued until the mixture was homogenous. The mixture was then coated onto a polyurethane film with a doctor blade and a silicone coated polyethylene film as a release liner was used to cover the composite. Within 30-60 minutes at room temperature, the tacky gel was not flowable and could be cut to size and packaged in a foil pouch. The gel composition was PVP/polyurethane of 1/1 at 20% solids.

The gel, when put into excess water, absorbed more liquid but did not dissolve or disintegrate. It could be heated, but did not break up even at the boiling point of water.

EXAMPLE 6

To a beaker containing 24 grams of 25% solids aqueous solution of PVP described in Example 3 was added 9.3 grams of distilled water with mechanical agitation. When the PVP was dispersed, 6.7 grams of Sancure 847 (30% solids) (Sanncor Industries), an aliphatic, water-dispersed urethane was added. After mixing so that uniform incorporation occurred, the mixture was cast onto a polypropylene diaper band scrim and doctored to a flat uniform thickness. A polyester film release liner was placed on top of the cast layer to form a composite. This allowed the fabric and tacky gel to stretch to make a well fitting bandage. The gel had a composition of PVP/polyurethane of 3/1 at 20% solids.

EXAMPLE 7

To a beaker containing 50.0 grams of a 20% solution of PVP described in Example 3 with agitation, 16.7 grams of distilled water and 1 gram of silver sulfadiazine were added. When this was thoroughly mixed, 32.3 grams of a water dispersed aromatic urethane NeoRex R-940 were added. Slow stirring was continued until mixed, and the mixture was cast on collagen film to which a release film was mated to form a composite. The tacky gel containing 1% silver sulfadiazine can be used as a burn dressing or an antimicrobial interface for a body-inserted medical device.

EXAMPLE 8

To a container was added 60.0 grams of a 20% solution of PVP described in Example 3 and 14.2 grams of distilled water. This was stirred to make a uniform solution. With slow agitation, 25.8 grams of a 31% solution of NeoRez R-940, an aqueous dispersion of an aromatic urethane made from TDI reacted with a dimethylolpropionic acid ethoxylate dispersed by making a salt with triethylamine, was added. Two slabs of gel were made; one on release liner and a second on a thin urethane film by coating a thick layer. The two slabs were allowed to gel at ambient temperature. Then a solution of six grams of salicyclic acid dissolved in 18 ml of ethanol was sprayed onto one slab of the gel and the alcohol allowed to evaporate. The two slabs were then pressed together with a roller to create a gel containing 6% salicyclic acid which can be used for corn removal pads which is an example of a drug delivery system coupled with the advantages of a tacky, hydrophilic gel.

EXAMPLE 9

To a beaker containing 22.7 gm of a 25% solution of PVP described in Example 3, with agitation, 15.0 gm of glycerine and 2.8 gm of distilled water were added. When this was thoroughly mixed, 9.5 gm of a water dispersed aliphatic urethane Sancure 847 (30% solids) was added. After mixing, it was coated onto a urethane film with an internal nylon scrim to a thickness of about 0.5-0.75 mm. At that point it had a composition of PVP/urethane of 2/1 at 17% solids. The coating was then dryed at 60° C. for about 10 minutes. The resultant gel contained about 45-50% of the original weight due to evaporation of water. At this point the gel had substantially stronger tack than before the drying step.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A dressing comprising a stable, tacky, hydrophilic gel which comprises a blend of polyurethane and a hydrophilic poly(N-vinyl lactam) having a K value calculated according to Finkentscher's formula of at least about 60 and above about 1.4 mole equivalents of available acid groups per mole of poly(N-vinyl lactam).

2. The dressing of claim 1 which further comprises at least one substrate.

3. The dressing of claim 1 wherein the poly(N-vinyl lactam) comprises polyvinylpyrrolidone homopolymer, copolymer or terpolymer.

4. The dressing of claim 1 wherein the gel comprises a poly(N-vinyl lactam)/polyurethane ratio of from about 75/1 to about 4/1.

5. The dressing of claim 1 wherein the gel further comprises an aqueous solution containing at least 5 weight percent poly(N-vinyl lactam) and polyurethane.

6. The dressing of claim 5 wherein the solution comprises water or a hydroalcohol.

7. The dressing of claim 1 wherein the poly(N-vinyl lactam) has mole equivalents of available acid groups of at least about 2.0.

8. The dressing of claim 2 wherein the substrate is selected from a group consisting of polymer film, silicone-polytetrafluorethylene film, collagen film, woven fabric, and non-woven fabric.

9. The dressing of claim 2 wherein the substrate is a polyurethane film.

10. The dressing of claim 2 wherein the substrate is a silicone-polytetrafluoroethylene film.

11. The dressing of claim 2 wherein the substrate is stretchable.

12. The dressing of claim 2 wherein one substrate is a release liner.

13. The dressing of claim 1 wherein the gel comprises at least one additional ingredient.

14. The dressing of claim 13 wherein the additional ingredient is glycerine or propylene glycol.

15. The dressing of claim 13 wherein the additional ingredient is releasable from the gel.

16. The dressing of claim 15 wherein the additional ingredient is a fragrance.

17. The dressing of claim 15 wherein the additional ingredient is a biologically active material having curative or therapeutic value for human or non-human animals.

18. The dressing of claim 17 wherein the additional ingredient is selected from a group consisting of nitroglycerine, scopalamine, pilocarpine, phenylpropanolamine, theophyline, tetracycline, neomycin, oxytetracycline, triclosan, sodium cefazolin, silver sulfadiazine, salicylates, nicotinates, capsaicin and benzocaine.

19. The dressing of claim 1 selected from a group consisting of wound dressings, burn dressings, drug delivery dressings, antimicrobial interface dressings for anchoring medical devices to the skin, sports wrap dressings, cosmetic mask dressings and cosmetic wrap dressings.

20. A stable, tacky, hydrophilic gel which comprises a blend of polyurethane and a hydrophilic poly(N-vinyl lactam) having a K value calculated according to Finkentscher's formula of at least about 60 and above about 1.4 mole equivalents of available acid groups per mole of poly(N-vinyl lactam), at least five weight percent polyurethane and poly(N-vinyl lactam) combined and a polyurethane/poly(N-vinyl lactam) ratio from about 0.5/1 to about 8/1 in an aqueous solution.

* * * * *